United States Patent [19]

Itoh et al.

[11] Patent Number: 4,552,865

[45] Date of Patent: Nov. 12, 1985

[54] PSYCHOTROPIC DRUGS

[75] Inventors: Shinji Itoh, Shiga; Takashi Moroji, Tokyo, both of Japan

[73] Assignee: Shionogi & Co., Ltd., Osaka, Japan

[21] Appl. No.: 628,964

[22] Filed: Jul. 11, 1984

Related U.S. Application Data

[63] Continuation of Ser. No. 503,646, Jun. 15, 1983, abandoned, which is a continuation of Ser. No. 293,265, Aug. 17, 1981, abandoned.

[30] Foreign Application Priority Data

Apr. 7, 1981 [JP] Japan ................................ 56-52551

[51] Int. Cl.$^4$ .............................................. A61K 37/02
[52] U.S. Cl. .................................................... 514/15
[58] Field of Search .................. 260/112.5 R; 424/177

[56] References Cited

U.S. PATENT DOCUMENTS 3,472,832 10/1969 Bernardi et al. ............. 260/112.5 R

OTHER PUBLICATIONS

Zetles, *Neuropharmacology*, 30, 277–283 (1981).
Hökfelt et al., *Nature*, 284, 515–521 (1980).
*Biological Abstracts*, 72 (4), 26487.
*Stedman's Medical Dictionary*, 23rd Ed., The Williams & Wilkins Co., Baltimore, pp. 1166 and 1259.

*Primary Examiner*—Delbert R. Phillips
*Assistant Examiner*—F. T. Mopzie
*Attorney, Agent, or Firm*—Wenderoth, Lind & Ponack

[57] ABSTRACT

Psychotropic drugs for treatment of psychoses containing caerulein or the pharmaceutically acceptable salts thereof as effective ingredient, and a method of treatment of psychoses comprising administering said drugs.

7 Claims, No Drawings

PSYCHOTROPIC DRUGS

This application is a continuation, of now abandoned application Ser. No. 503,646, filed June 15, 1983 which application is a continuation of now abandoned application Ser. No. 293,265, filed Aug. 17, 1981.

BACKGROUND OF THE INVENTION

Caerulein is a decapeptide which has been discovered in the skin of an Australian amphibian, Hyla caerulea, of which the chemical structure resembles that of cholecystokinin, and stimulates contraction of the gallbladder, secretion of the pancreatic juice, motion of the intestine, and secretion of the gastric juice. The complete structure of caerulein has been elucidated, and the chemically synthetic route has also been established. [A. Anastasi, V. Erspamer and R. Endean, Experientia, 23, 699 (1967); L. Bernardi, G. Bosisio, R. de Castiglione and O. Goffredo, Ibid., 23, 700; V. Erspamer, G. Bertaccini, G. de Caro, R. Endean and M. Impicciatore, Ibid., 23, 702].

The chemical name of caerulein is: 5-oxo-L-prolyl-L-glutaminyl-L-aspartyl-O-sulfo-L-tryosyl-L-threonylglycyl-L-tryptophyl-L-methionyl-L-aspartyl-L-phenylalaninamide.

The toxicity of caerulein has been investigated in detail [Chieli, T. et al., Toxico, and Pharmaco., 23, 480 (1972); Miyazaki et al., Kiso to Rinsho in Japan, 8, no. 7, 98 (1974)]; acute toxicity in mice (intravenous), $LD_{50}=647$ mg/kg in male and 702 mg/kg in female; in rats (intravenous), $LD_{50}=714$ mg/kg in male and 571 mg/kg in female.

SUMMARY OF THE INVENTION

The present invention relates to new psychotropic drugs containing caerulein or the pharmaceutically acceptable salts thereof as effective ingredient, and a method of treatment of psychoses comprising administering said drugs.

The present inventors have noticed that the caerulein-like peptides are found in the central nervous system, particularly in the carebral cortex in abundance, and show apparent physiological actions, and the inventors have had intention of developing caerulein as psychotropic drugs. As a result, the present inventors have found that caerulein when administered to humans improves rapidly and markedly the mental conditions, and completed the present invention.

The psychotropic drugs provided by the present invention can be used as drugs acting on a wide variety of psychoses, of which the action is dependent on the CNS action of caerulein. Particularly, the drugs are effective in treatment of functional psychoses including schizophrenia, mania, depression, psychoneurosis, and so on, and of senile psychoses such as cerebral arteriosclerosis, senile dementia, etc. In this invention caerulein itself or its pharmaceutically acceptable salts (e.g. tris-diethylamine salt) may be employed. Caerulein occurs as a natural product as described above, and it can also be synthesized chemically (for instance, Experientia, 23, 700 (1967)).

The following are cases in which the drug of the present invention has clinically been applied to the patients of schizophrenia.

(1) Method of application: Caerulein tris-diethylamine salt is dissolved in sterilized physiological saline at a rate of 20 μg/ml (W/V), and intramuscularly injected to each patient once at a dose of 0.3 μg/kg (body weight) or 0.6 μg/kg (body weight).

Table 1 shows types of the patients tested and medication.

(2) Test result: Table 2 shows the antipsychotic effect and side effect after the injection.

TABLE 1

| P.N.[1] | Sex[2] | Age | Disease Diagnosed | Stage of Illness | Condition | $T_1$[3] | Fr.[4] | $T_2$[5] | Drug Used Together |
|---|---|---|---|---|---|---|---|---|---|
| 1 | W | 44 | Schizophrenia (Hebephrenia) | Chronic (Defect) | Hallucination Delusion Lack of Spontaneity | 27 yrs. | 4 | 5 yrs. 5 mons. | Oxypertine 120 mg Levomepromazine 150 mg |
| 2 | W | 48 | Schizophrenia (Hebephrenia) | Chronic (Defect) | Hallucination Delusion Hypochondria Lack of Spontaneity | 20 yrs. | 1 | 17 yrs. 11 mons. | Oxypertine 240 mg |
| 3 | W | 36 | Schizophrenia (Delusional) | Chronic (Defect) | Hallucination Lack of Spontaneity | 13 yrs. | 3 | 5 yrs. 4 mons. | Oxypertine 120 mg |
| 4 | W | 22 | Schizophrenia (Delusional) | Chronic Advanced Stage | Hallucination Delusion Negativism | 2 yrs. | 3 | 1 mon. | Haloperidol 27 mg Levomepromazine 150 mg |
| 5 | W | 33 | Schizophrenia (Delusional) | Chronic (Defect) | Hallucination Delusion Incoherence | 5 yrs. 9 mons. | 1 | 5 yrs. 8 mons. | Oxypertine 120 mg Sulpiride 300 mg |
| 6 | M | 36 | Schizophrenia (hebephrenia) | Chronic (Defect) | Hallucination Lack of Spontaneity | 18 yrs. | 3 | 11 mons. | Oxypertine 120 mg Vegetamin B[6] 2 tablets |
| 7 | M | 40 | Schizophrenia (Delusional) | Chronic (Defect) | Hallucination Lack of Spontaneity | 20 yrs. | 4 | 6 mons. | Oxypertine 180 mg |
| 8 | M | 31 | Schizophrenia (Hebephrenia) | Chronic (Defect) | Hallucination Blunted affect Lack of Spontaneity | 6 yrs. | 3 | 5 mons. | Oxypertine 120 mg |
| 9 | M | 39 | Schizophrenia (Delusional) | Chronic (Defect) | Delusion Incoherence | 20 yrs. | 5 | 5 yrs. 4 mons. | Oxypertine 80 mg Vegetamin B 1 tablet |
| 10 | M | 41 | Schizophrenia (Hebephrenia) | Chronic (Defect) | Incoherence Austim | 24 yrs. | 3 | 5 yrs. 5 mons. | Propericiazine 30 mg Levomepromazine 150 mg Oxypertine 300 mg Haloperidol 27 mg |
| 11 | M | 38 | Schizophrenia (Delusional) | Chronic (Defect) | Hallucination Delusion | 9 yrs. | 5 | 1 yr. 4 mons. | Haloperidol 6 mg |
| 12 | M | 45 | Schizophrenia | Chronic | Delusion | 3 yrs. | 2 | 7 mons. | Oxypertine 160 mg |

TABLE 1-continued

| P.N.[1] | Sex[2] | Age | Disease Diagnosed | Stage of Illness | Condition | T₁[3] | Fr.[4] | T₂[5] | Drug Used Together |
|---|---|---|---|---|---|---|---|---|---|
| | | | (Delusional) | (Defect) | Lack of Spontaneity | | | | |

Notes:
[1]Patient Number
[2]M: Man; W: Woman
[3]Term of Illness
[4]Frequency of Attack
[5]Term Passed Before Administration
[6]One tablet contains 12.5 mg chlorpromazine hydrochloride, 12.5 mg prometazine hydrochloride, and 30 mg phenobarbital.

TABLE 2

| | Change of Subjective Symptom | | Judgement of clinical effect on each symptom[2] | | | | | | | | | |
|---|---|---|---|---|---|---|---|---|---|---|---|---|
| No.[1] | 0.3 μg/kg (Injection) | 0.6 μg/kg (Injection) | I | II | III | IV | V | VI | VII | VIII | IX | Side effect |
| 1 | Calmness; sensation of moving from "dark" to "bright" place; light sensation in body | Calmness; broad-mindedness; more pleasant sensation; auditory hallucinations reduced 2-3 mins. after the injection; refreshed sensation | ++ | + | + | ++ | + | + | ++ | + | ++ | No |
| 2 | Sleepiness (during the menstruation) | Auditory hallucinations reduced; disappearence of extracampine hallucination; singing voice heard alone; vaguely fine. | ++ | + | + | ++ | ++ | ++ | ++ | ++ | ++ | After 30 mins., a short term pain at the epigastric region. |
| 3 | No change | No change; slightly less fatigue. | ++ | ++ | ++ | + | O | O | O | + | ++ | Abdominal pain and a motion |
| 4 | No change | No change | O | O | O | O | O | O | O | O | O | Borborygmus 1 hr. after injection. |
| 5 | Sensation that weight has been lifted off chest | Light sensations in body; accusing voice (auditory hallucination) disappeared. | + | O | + | + | + | + | + | + | + | No |
| 6 | Head refreshed Cheerful sensation | Refreshed; light sensation in body (After 1 hr. from the injection I felt the auditory hallucination was slightly diminished.) | + | + | O | ++ | O | + | O | + | + | No |
| 7 | No change | Little change; slightly relaxed; auditory hallucination less irritating. | ++ | O | O | + | O | + | + | + | ++ | No |
| 8 | No change | Much refreshed; baresthesia reduced; head refreshed; no change in auditory hallucination. | O | O | O | O | O | O | O | + | ++ | No |
| 9 | Pleasant sensation Calmness; less anxiety | Refreshed immediately after the injection; bracing and good feeling; sensation of head muddled and body languid. | ++ | O | + | + | + | + | + | + | ++ | No |
| 10 | Refreshed sensation Relieved | Tension relaxed; relieved; less confined | O | O | O | + | O | + | + | + | + | No |
| 11 | No change. Auditory hallucinations reduced | Refreshed, relaxed sensations (I've never felt this way before, I feel pressure on my chest.) | + | O | O | + | + | O | O | ++ | ++ | No |
| 12 | No change | No change | O | O | O | O | O | O | O | O | O | No |

Notes:
[1]Patient Number
[2]I: Hallucination and dilusion (abnormal experience).
II: Self-disorder.
III: Thought disorder.
IV: Rapport.
V: Speech (increase or decrease).
VI: Motor activity (unnatural, increase or decrease).
VII: Behavior in the hospital.
VIII: Social behavior.
IX: Emotional disturbance
++: Marked improvement +: Improvement O: No change —: Change for the worse As shown in Table 2, the psychotropic drug of the present invention improved greatly the condition of chronic patients of schizophrenia at a single dose of 0.3 μg/kg or 0.6 μg/kg. The drugs have similar therapeutic effects on other type of psychoses, and can be used widely as psychotropic drugs.

As far as caerulein is absorbed without being decomposed to exhibit the therapeutic effect, the drugs may be administered through any route of application. In view of the properties of caerulein, it is particularly appropriate to administer it parenterally (for instance as injections or suppositories), usually as intramuscular injections. Additionally, it is also appropriate to administer in recently clinically applied systems for releasing at retard the implanted drugs, in which a pellet or reservoir is implanted in the body so that caerulein is released stationarily.

The preparation of the drugs may be made in a conventional manner using usually employed bases and pharmaceutical technics. For instance, liquid preparations including solutions and suspensions may be prepared together with aquatic solvents (e.g. distilled water, physiological saline, Ringer's solution, 5% glucose solution) of non-aquatic solvents (e.g. peanut oil, sesame oil, olive oil, tsubaki oil, apricot oil, soybean oil, mono or diglyceride, glycerin 1,3-diethyl ether, methyl acetamide, various kind of glycols, glycerin). The suppositories may be prepared together with conventional bases for suppositories (e.g. cacao butter, Witepsol (trade name), Novata (trade name), various kinds of carbowax or polyethylene glycol, glycerogelatin, glycerin, purified lanolin) and gelatin capsules. In preparing the preparations, it is appropriate to use conventional additives such as stabilizers, dispersants, buffers, antiseptics, or colouring agents, and if required it is also appropriate to add additional drugs such as antipsychotics, antianxiety agents, antidepressants, hypnotics, antiepileptics, analgesics, local anesthetics, nutrition aids, or vitamins.

The dose of the drugs are variable in accordance with the sex, age, condition or medical record of patients as well as the route or purpose of the administration. In general, the drugs may be administered at a single or divided doses of about 0.1–1000 μg/kg body weight a day as effective ingredient, preferably about 0.2–100 μg/kg body weight, more preferably 0.3–60 μg/kg body weight.

The following examples serve to illustrate but are not intended to limit the scope of the invention.

EXAMPLE 1

Caerulein tris-diethylamine salt—0.3 mg
Sodium chloride—90 mg
The whole is made to 10 ml with distilled water for injection.

The above components are dissolved completely, filtered under sterile condition, and divided into 10 ampoules to give injection preparations.

EXAMPLE 2

Caerulein tris-diethylamine salt—0.5 mg
Glucose—500 mg
The whole is made to 10 ml with distilled water for injection.

Treatment in the same manner as in Example 1 gives injection preparation.

EXAMPLE 3

Caerulein tris-diethylamine salt—6 mg
Xylocaine—250 mg
Citrate buffer—100 ml
The above components are dissolved completely and treated in the same manner as in Example 1 to give 100 ampoules for injection.

EXAMPLE 4

Caerulein tris-diethylamine salt—0.6 mg
Water—1 g
Gelatin—2 g
Glycerin—7 g
Water, gelatin and glycerin are dissolved under warming, and caerulein tris-diethylamine salt is added, dispersed with stirring, and formulated into 10 pieces of suppositories.

EXAMPLE 5

Caerulein tris-diethylamine salt—10 mg
Carbowax 1000—96 g
Carbowax 4000—4 g
Carbowax 1000 and Carbowax 4000 are dissolved under warming and treated in the same manner as in Example 4 to give 100 pieces of suppositories.

EXAMPLE 6

Caerulein tris-diethylamine salt—50 mg
Liquid paraffin—25 g
Cacao butter—500 g
Caerulein tris-diethylamine salt is dissolved in liquid paraffin with stirring, then added and dispersed with stirring into cacao butter melted under warming, and formulated into 500 pieces of suppositories.

EXAMPLE 7

In Example 6, liquid paraffin and cacao butter are employed in place of 525 g of Witepsol H 35 (trade name), and formulated into 500 pieces of suppositories.

EXAMPLE 8

Caerulein tris-diethylamine salt—0.2 mg
Mannitol—300 mg
Sodium thiomalate—5 mg
Sodium hydroxide—proper amount
Caerulein tris-diethylamine salt, mannitol and sodium thiomalate are dissolved in distilled water for injection and adjusted at pH 7.0 with sodium hydroxide. The whole is made to 10 ml with distilled water and divided into 10 ampoules to give injection preparations.

What is claimed is:

1. A method of treatment of schizophrenia which comprises administering an effective amount of caerulein or a pharmaceutically acceptable salt thereof to a subject requiring that treatment.

2. A method as claimed in claim 1, wherein the psychosis is schizophrenia.

3. A method as claimed in claim 1, wherein the effective amount is 0.1–1000 μg.

4. A method as claimed in claim 1, wherein the effective amount is 0.2–100 μg.

5. A method as claimed in claim 1, wherein the effective amount is 0.3–60 μg.

6. A method as claimed in claim 1, wherein the salt is the tris-diethylamine salt.

7. A method as claimed in claim 1, wherein the administering is effected by intramuscular injection.

* * * * *